(12) United States Patent
Kopelman et al.

(10) Patent No.: US 9,983,110 B2
(45) Date of Patent: May 29, 2018

(54) ASYNCHRONOUS MAGNETIC BEAD ROTATION (AMBR) MICROVISCOMETER FOR ANALYSIS OF ANALYTES

(71) Applicant: THE REGENTS OF THE UNIVERSITY OF MICHIGAN, Ann Arbor, MI (US)

(72) Inventors: Raoul Kopelman, Ann Arbor, MI (US); Mark A. Burns, Ann Arbor, MI (US); Yunzi Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 572 days.

(21) Appl. No.: 14/532,907

(22) Filed: Nov. 4, 2014

(65) Prior Publication Data

US 2015/0140560 A1 May 21, 2015

Related U.S. Application Data

(60) Provisional application No. 61/899,660, filed on Nov. 4, 2013.

(51) Int. Cl.
*C12Q 1/68* (2018.01)
*G01N 11/16* (2006.01)
*G01N 11/10* (2006.01)
*G01N 11/00* (2006.01)

(52) U.S. Cl.
CPC ......... *G01N 11/165* (2013.01); *C12Q 1/6816* (2013.01); *G01N 11/10* (2013.01); *G01N 2011/0086* (2013.01)

(58) Field of Classification Search
None
See application file for complete search history.

(56) References Cited

U.S. PATENT DOCUMENTS

| | | |
|---|---|---|
| 3,676,679 A | 7/1972 | Waters |
| 3,687,808 A | 8/1972 | Merigan et al. |
| 4,778,758 A | 10/1988 | Ericsson et al. |
| 5,171,534 A | 12/1992 | Smith et al. |
| 5,232,839 A | 8/1993 | Eden et al. |
| 5,252,493 A | 10/1993 | Fujiwara et al. |
| 5,293,210 A | 3/1994 | Berndt |
| 5,336,600 A | 8/1994 | Monget |
| 5,374,527 A | 12/1994 | Grossman |
| 5,432,272 A | 7/1995 | Benner |
| 5,434,056 A | 7/1995 | Monget et al. |
| 5,516,670 A | 5/1996 | Kuehnle et al. |
| 5,534,527 A | 7/1996 | Black et al. |
| 5,593,854 A | 1/1997 | Berndt |
| 5,716,798 A | 2/1998 | Monthony et al. |
| 5,770,388 A | 6/1998 | Vorpahl |
| 5,770,440 A | 6/1998 | Berndt |
| 5,814,474 A | 9/1998 | Berndt |
| 5,888,760 A | 3/1999 | Godsey et al. |
| 5,910,300 A | 6/1999 | Tournier et al. |
| 5,998,224 A | 12/1999 | Rohr et al. |
| 5,998,517 A | 12/1999 | Gentle, Jr. et al. |
| 6,002,817 A | 12/1999 | Kopelman et al. |
| 6,027,946 A | 2/2000 | Weitschies et al. |
| 6,096,272 A | 8/2000 | Clark et al. |
| 6,107,102 A | 8/2000 | Ferrari |
| 6,143,558 A | 11/2000 | Kopelman et al. |
| 6,159,686 A | 12/2000 | Kardos et al. |
| 6,275,031 B1 | 8/2001 | Simmonds |
| 6,372,485 B1 | 4/2002 | Clark et al. |
| 6,395,506 B1 | 5/2002 | Pitner et al. |
| 6,437,563 B1 | 8/2002 | Simmonds et al. |
| 6,518,747 B2 | 2/2003 | Sager et al. |
| 6,586,259 B1 | 7/2003 | Mahan et al. |
| 6,596,532 B1 | 7/2003 | Hyman et al. |
| 6,597,176 B2 | 7/2003 | Simmonds et al. |
| 6,632,655 B1 | 10/2003 | Mehta et al. |
| 6,660,381 B2 | 12/2003 | Halas et al. |
| 6,777,226 B2 | 8/2004 | Jeffrey et al. |
| 6,780,581 B2 | 8/2004 | Vesey et al. |
| 6,825,655 B2 | 11/2004 | Minchole et al. |
| 6,900,030 B2 | 5/2005 | Pitner et al. |
| 6,927,570 B2 | 8/2005 | Simmonds et al. |

(Continued)

FOREIGN PATENT DOCUMENTS

WO WO-00/067037 A2 11/2000
WO WO-01/014591 A1 3/2001
(Continued)

OTHER PUBLICATIONS

Agayan et al., Optical Manipulation of Metal-Silica Hybrid Nanoparticles, *Proceedings of SPIE*, 5514:502-513 (2004).
Anker et al., Magnetically Modulated Optical Nanoprobes, *Appl. Phys. Letts.*, 82:1102-1104 (2003).
Astalan et al., Biomolecular Reactions Studied Using Changes in Brownian Rotation Dynamics of Magnetic Particles, *Biosensors and Bioelectronics*, 19:945-951 (2004).
Bao et al., Cell and Molecular Mechanics of Biological Materials, *Nat. Mat.*, 2:715-725 (2003).
Behrend et al., Brownian Modulated Optical Nanoprobes, *Appl. Phys. Letts.*, 84:154-156 (2004).

(Continued)

*Primary Examiner* — David C Thomas
(74) *Attorney, Agent, or Firm* — Marshall, Gerstein & Borun LLP

(57) ABSTRACT

The disclosure provides a label-free viscosity-based analyte detection system using paramagnetic beads as an asynchronous magnetic bead rotation (AMBR) microviscometer. It is disclosed herein that the bead rotation period is linearly proportional to the viscosity of a solution comprising analytes surrounding the paramagnetic bead. Optical measurement of asynchronous microbead motion determines solution viscosity precisely in microscale volumes, thus allowing an estimate of analyte concentration. The results demonstrate the feasibility of viscosity-based analyte detection using AMBR in microscale aqueous volumes.

23 Claims, 7 Drawing Sheets

(56) References Cited

U.S. PATENT DOCUMENTS

| | | | |
|---|---|---|---|
| 7,115,384 | B2 | 10/2006 | Clark et al. |
| 7,183,073 | B2 | 2/2007 | Hyman et al. |
| 7,323,139 | B2 | 1/2008 | LaBorde et al. |
| 7,341,841 | B2 | 3/2008 | Metzger et al. |
| 7,547,554 | B2 | 6/2009 | Odefey |
| 7,564,245 | B2 | 7/2009 | Lee |
| 7,575,934 | B2 | 8/2009 | Atwood |
| 7,691,600 | B2 | 4/2010 | Mercader Badia et al. |
| 8,846,331 | B2 | 9/2014 | McNaughton et al. |
| 2002/0150914 | A1 | 10/2002 | Andersen et al. |
| 2003/0012693 | A1 | 1/2003 | Otillar et al. |
| 2003/0076087 | A1 | 4/2003 | Minchole et al. |
| 2003/0124516 | A1 | 7/2003 | Chung et al. |
| 2003/0169032 | A1 | 9/2003 | Minchole et al. |
| 2004/0033627 | A1 | 2/2004 | Aytur et al. |
| 2004/0058458 | A1 | 3/2004 | Anker et al. |
| 2005/0048672 | A1 | 3/2005 | Luxton et al. |
| 2006/0008924 | A1 | 1/2006 | Anker et al. |
| 2006/0057578 | A1 | 3/2006 | Willner et al. |
| 2006/0160171 | A1 | 7/2006 | Bachur et al. |
| 2006/0210987 | A1 | 9/2006 | Gleich |
| 2007/0020720 | A1 | 1/2007 | Colin et al. |
| 2007/0037225 | A1 | 2/2007 | Metzger et al. |
| 2007/0205767 | A1 | 9/2007 | Xu et al. |
| 2008/0038769 | A1 | 2/2008 | Bernardi et al. |
| 2008/0220411 | A1 | 9/2008 | McNaughton et al. |
| 2009/0085557 | A1 | 4/2009 | Krozer et al. |
| 2009/0136953 | A1 | 5/2009 | Gold et al. |
| 2009/0269854 | A1 | 10/2009 | Kageyama |
| 2010/0033158 | A1 | 2/2010 | Dittmer et al. |
| 2010/0068755 | A1 | 3/2010 | Walsh et al. |
| 2010/0072994 | A1 | 3/2010 | Lee et al. |
| 2010/0129857 | A1 | 5/2010 | Walsh et al. |
| 2012/0164680 | A1 | 6/2012 | McNaughton et al. |

FOREIGN PATENT DOCUMENTS

| | | | |
|---|---|---|---|
| WO | WO-03/019188 | A1 | 3/2003 |
| WO | WO-2006/104700 | A1 | 10/2006 |
| WO | WO-2007/120095 | A1 | 10/2007 |
| WO | WO-2008/075285 | A1 | 6/2008 |
| WO | WO-2009/037636 | A1 | 3/2009 |
| WO | WO-2010/026551 | A1 | 3/2010 |
| WO | WO-2010/041178 | A1 | 4/2010 |
| WO | WO-2010/048511 | A1 | 4/2010 |
| WO | WO-2011/021142 | A1 | 2/2011 |
| WO | WO-2012/027747 | A2 | 3/2012 |

OTHER PUBLICATIONS

Behrend et al., Microheology with Modulated Optical Nanoprobes (MOONs), *J. Magnetism and Magnetic Mats.*, 293:663-670 (2005).
Bhiladvala et al., Effect of Fluids on the Q Factor and Resonance Frequency of Oscillating Micrometer and Nanometer Scale Beams, *Phys. Rev. E*, 69:36307-1-36307-5 (2004).
Biswal et al., Micromixing with linked chains of paramagnetic particles, *Anal. Chem.*, 76:6448-55 (2004).
Bornhop et al., Advance in contrast agents, reporters, and detection, *J.Biomed. Optics*, 6(2):106-115 (2001).
Boucher et al., Bad bugs, no drugs: no ESKAPE! An update from the Infectious Diseases Society of America, Clin. Infect. Dis., 48(1):1-12 (2009).
Boucher et al., Epidemiology of methicillin-resistant *Staphylococcus aureus*, Clin. Infect. Dis., 46 Suppl 5:S344-9 (2008).
Cebers, Dynamics of an Active Magentic Particle in a Rotating Magentic Field, *Phys. Rev. E.*, 73:021505-1-021505-5 (2006).
Chevry et al., Magnetic wire-based sensors for the microrheology of complex fluids, Phys. Rev. E, 88:062306 (2013).
Chu et al., *Staphylococcus aureus* bacteremia in patients with prosthetic devices: costs and outcomes, Am. J. Med., 118(12):1416 (2005).
Connolly et al., Experimental evaluation of the magnetic properties of commercially available magnetic microspheres, Biomed. Mater. Eng., 15(6):421-31 (2005).
Cook, Medicinal chemistry of antisense oligonucleotides—future opportunities. Anticancer Drug Des., 6(6):585-607 (1991).
Cragg et al., Shear dependence in the viscometry of high polymer solutions: a new variable-shear capillary viscometer, Can. J. Chem., 39(1):203-15 (1961).
Crick, The Physical Properties of Cytoplasm. A Study by Means of the Magnetic Particle Method. Part II. Theoretical Treatment, Strangeways Research Laboratory, Cambridge, 505-532 (1950).
Crick, et al., The Physical Properties of Cytoplasm a Study by Means of the Magnetic Particle Method—Part I Experimental, Strangeways Research Laboratory, 37-80 (1949).
Deresinski, Counterpoint: Vancomycin and *Staphylococcus aureus*—an antibiotic enters obsolescence, Clin. Infest. Dis., 44(12):1543-8 (2007).
Descamps et al., Functionalization of optical nanotip arrays with an electrochemical microcantilever for multiplexed DNA detection, Lab on a Chip, 13:2956-62 (2013).
Diakite et al., A low-cost, label-free DNA detection method in lab-on-chip format based on electrohydrodynamic instabilities, with application to long-range PCR, Lab Chip, 12(22):4738-47 (2012).
Ekinci et al., Nanoelectromechnical Systems, *Review of Scientific Instruments*, 76:061101-1-061101-12 (2005).
Elbez et al., Nanoparticle induced cell magneto-rotation: monitoring morphology, stress and drug sensitivity of a suspended single cancer cell, PLOS One, 6(12):e28475 (2011).
Elfwing et al., Observing Growth and Division of Large Numbers of Individual Bacteria by Image Analysis, *Applied and Environmental Microbiology*, 70(2):675-678 (2004).
Englisch et al., Chemically modified oligonucleotides as probes and inhibitors, Angew. Chem. Int. Ed. English, 30: 613-29 (1991).
Fennimore et al., Rotational Actuators based on Carbon Nanotubes, *Nature*, 424:408-410 (2003).
Fratamico et al., Detection of *Escherichia coli* 0157:H7 using a surface plasmon resonance biosensor, Biotechnology Techniques, 12(7):571-6 (1998).
Freier et al., The ups and downs of nucleic acid duplex stability: structure-stability studies on chemically-modified DNA:RNA duplexes, Nucleic Acids Res., 25(22):4429-43 (1997).
Frka-Petesic et al., Dynamics of paramagnetic nanostructured rods under rotating field, J. Magn. Magn. Mater., 323(10):1309-13 (2011).
Fujinami et al., Sensitive detection of bacteria and spores using a portable bioluminescence ATP measurement assay system distinguishing from white powder materials, J. Health Sci., 50:126-32 (2004).
Gfeller et al., Micromechanical oscillators as rapid biosensor for the detection of active growth of *Escherichia coli*, Biosens. Biolectron., 21(3):528-33 (2005).
Gitterman et al., Order and Choas: Are They Contradictory or Complementary? *Eur. J. Phys.*, 23:119-122 (2002).
Godin et al., Using buoyant mass to measure the growth of single cells, Nat. Methods, 7(5):387-90 (2010).
Gu et al., Using Biofunicational Magnetic Nanoparticles to Capture Gram-Negative Bacteria at an Ultra-Low Concentration, *Chemical Communications*, 15:1966-1967 (2003).
Hafeli et al., Characterization of Magnetic Particles and Microspheres and Their Magnetophoretic Mobility Using a Digital Microscopy Method, *European Cells and Materials*, 3:24-27 (2002).
Handal et al., DNA mutation detection and analysis using miniaturized microfluidic systems, Expert. Rev. Mol. Diagn., 6(1):29-38 (2006).
Haukanes et al., Application of Magnetic Beads in Bioassays, *Bio-Technology*, 11:60-63 (1993).
Hecht et al., Bead assembly magnetorotation as a signal transduction method for protein detection, Biosens. Bioelectron., 48:26-32 (2013).
Helgesen et al., Dynamic behavior of simple magnetic hole system, Phys. Rev. A, 42:7271-80 (1990).

(56) References Cited

OTHER PUBLICATIONS

Helgesen et al., Nonlinear phenomena in systems of magnetic holes, Phys. Rev. Lett., 64(12):1425-8 (1990).
Heo et al., The scaling of zero-shear viscosities of semidilute polymer solutions with concentration, J. Rheol., 49:1117 (2005).
Horvath et al., Magnetic Dimer Motion Effects in a Rotating Magnetic Field (A Qualitative Model of Magnetoviscosity and Permittivity in Magnetorheological Suspensions), Czech J. Phys., 43:671-681 (1993).
Huggins, The Viscosity of Dilute Solutions of Long-Chain Molecules. IV. Dependence on Concentration, J. Am. Chem. Soc., 64(11):2716-8 (1942).
Hulteen et al., Nanosphere Lithography: A Materials General Fabrication Process for Periodic Particle Array Surfaces, *J. Vac. Sci. Technol. A.*, 13:1553-1558 (1995).
Ilic et al., Single Cell Detection with Micromechanical Oscillators, *J. Vacuum Sci. & Tech. B: Microelectronics and Nanometer Structures*, 19:2825-2828 (2001).
Ilic et al., Virus Detection Using Nanoelectromechanical Devices, *Appl. Phys. Lett.*, 85:2604-2606 (2004).
Ilic et al., Mechanical resonant immunospecific biological detector, Appl. Phys. Lett., 77:450-2 (2000).
Ishiyama et al., Swimming of Magnetic Micro-Machines under a Very Wide-Range of Reynolds Number Conditions, *IEEE Trans. Magn.*, 37(4):2868-2870 (2001).
Jain, Understanding barriers to drug delivery: high resolution in vivo imaging is key, *Clinical Cancer Research*, 5(7):1605-1606 (1999).
Janssen et al., Controlled torque on superparamagnetic beads for functional biosensors, Biosens. Bioelectron., 24(7):1937-41 (2009).
Jiang et al., A lost-wax approach to monodisperse colloids and their crystals, *Science*, 291:453-457 (2001).
Kashevsky, Nonlinear Flow-Particle Interaction in Suspensions of Fine Quasi-Rigid Ferroparticles: A Giant Magnetic Effect of Fluid Rotation, *J. Phys. D: AppL Phys.*, 34:518-524 (2001).
Kinnunen et al., Monitoring the growth and drug susceptibility of individual bacteria using asynchronous magnetic bead rotation sensors, Biosens. Bioelectron., 26(5):2751-5 (2011).
Kinnunen et al., Self-Assembled Magnetic Bead Biosensor for Measuring Bacterial Growth and Antimicrobial Susceptibility Testing, Small, 8(16):2477-82 (2012).
Klevens et al., Changes in the epidemiology of methicillin-resistant *Staphylococcus aureus* in intensive care units in US hospitals, 1992-2003, Clin. Infest. Dis., 42(3):389-91 (2006).
Kneipp et al., Surface-Enhanced Raman Spectroscopy in Single Living Cells Using Gold Nanoparticles , *Applied Spectroscopy*, 56(2):150-154 (2002).
Korneva et al., Carbon Nanotubes Loaded with Magnetic Particles, *Nano Lett.*, 5:879-884 (2005).
Koskinen et al., Development of a rapid assay methodology for antimicrobial susceptibility testing of *Staphylococcus aureus*, Diagn. Microbiol. Infect. Dis., 62(3):306-16 (2008).
Kroschwitz (Ed.), The Concise Encyclopedia of Polymer Science and Engineering, pp. 858-859, John Wiley & Sons (1990).
Kubista et al., The real-time polymerase chain reaction, Mol. Aspects Med., 27(2-3):95-125 (2006).
Kumar et al., Duration of hypotension before initiation of effective antimicrobial therapy is the critical determinant of survival in human septic shock, Crit. Care Med., 34(6):1589-96 (2006).
Kurlyandskaya et al., Magnetic Dynabeads Detection by Sensitive Element Based on Giant Magnetoimpedance, *Biosensors and Bioelectronics*, 20:1611-1616 (2005).
Landegren et al., DNA diagnostics—molecular techniques and automation, Science, 242(4876):229-37 (1988).
Lapointe et al., Statis and Dynamic Properties of Magnetic Nanowires in Nematic Fluids, *J. Appl. Phys.*, 97:10 (2005).
Leslie et al., New detection modality for label-free quantification of DNA in biological samples via superparamagnetic bead aggregation, J. Am. Chem. Soc., 134(12):5689-96 (2012).
Li et al., Asynchronous Magnetic Bead Rotation (AMBR) Microviscometer for Label-Free DNA Analysis, Biosensors (Basel), 4(1):76-89 (2014).
Li et al., Asynchronous Magnetic Bead Rotation (AMBR) Viscometer for Label-Free DNA Detection in Digestion and Quantitative PCR, AiChE 2013 Annual Meeting (Nov. 5, 2013).
Li et al., Quantitative and rapid DNA detection by laser transmission spectroscopy, PLoS One, 6(12):e29224 (2011).
Livak-Dahl et al., Nanoliter droplet viscometer with additive-free operation, Lab Chip, 13(2):297-301 (2013).
Lu et al., Nanophotonic Crescent Moon Structures with Sharp Edge for Ultrasensitive Biomolecular Detection by Local Electromagnetic Field Enhancement Effect, *Nano Lett.*, 5:119-124 (2005).
MacDougall et al., Antimicrobial stewardship programs in health care systems, Clin. Microbiol. Rev., 18(4):638-56 (2005).
Mandal et al., Methods for rapis detection of foodborne pathogens: An overview, Am. J. Food Technol., 6: 87-102 (2011).
Mathur et al., A New FRET-Based Sensitive DNA Sensor for Medical Diagnostics using PNA Probe and Water-Soluble Blue Light Emitting Polymer, J. Sensors, 2008: Article ID 270475 (2008).
Mayer et al., Measurement of the Fluorescence Lifetime in Scattering Media by Frequency-Domain Photon Migration , *Applied Optics*, 38:4930-4938 (1999).
McNaughton et al. Sudden Breakdown in Linear Response of a Rotationally Driven Magnetic Microparticle and Application to Physical and Chemical Microsensing (J. Phys. Chem. B, 110 (38), pp. 18958-18964 (2006).
McNaughton et al., Fabrication of Uniform Half-Shell Magnetic Nanoparticles and Microspheres with Applications as Magnetically Modulated Optical Nanoprobes, arXiv:cond-mat/0506418v1, pp. 1-6 (2005).
McNaughton et al., Compact sensor for measuring nonlinear rotational dynamics of driven magnetic microspheres with biomedical applications, JMMM, 321:1648-52 (2009).
McNaughton et al., Physiochemical microparticle sensors based on nonlinear magnetic oscillations, Sens. Actuators B, 121(1):330-40 (2007).
McNaughton et al., Single bacterial cell detection with nonlinear rotation rate shifts of driven magnetic microspheres, Appl. Phys. Lett., 91:224105 (2007).
Melle et al., Structure and dynamics of magnetorheological fluids in rotating magnetic fields, Phys. Rev. E, 61(4):4111-7 (2000).
Merkt et al., Capped Colloids as Light-Mills in Optical Traps, arXiv:cond-mat/0605463v1, pp. 1-10 (2006).
Metzger, Amorphous Whiskers of a Cobalt-Gold Alloy, *Nature*, 212:176-177 (1966).
Moller et al., Ultrafine particles cause cytoskeletal dysfunctions in macrophages, *Toxicology and Applied Pharmacology*, 182(3):197-207 (2002).
National Nosocomial Infections Surveillance System, National Nosocomial Infections Surveillance (NNIS) System Report, data summary from Jan. 1992 through Jun. 2004, issued Oct. 2004, Am. J. Infect. Control., 32(8):470-85 (2004).
Newman et al., Motions of a Magnetic Particle in a Viscous Medium, *J. Appl. Phys.*, 39:5566-5569 (1968).
Nie et al., Probing Single Molecules and Single Nanoparticles by Surface-Enhanced Raman Scattering, *Science*, 275(5303):1102-1106 (1997).
Noskin et al., National trends in *Staphylococcus aureus* infection rates: impact on economic burden and mortality over a 6-year period (1998-2003), Clin. Infect. Dis., 45(9):1132-40 (2007).
Nozawa et al., Smart Control of Monodisperse Stöber Silica Particles: Effect of Reactant Addition Rate on Growth Process, *Langmuir*, 21:1516-1523 (2005).
Olsvik et al., Magnetic Separation Techniques in Diagnostic Microbiology, *Clinical Microbiology Reviews*, 7:43-54 (1994).
Paul et al., Stochastic Dynamics of Nanoscale Mechanical Oscillators Immersed in a Viscous Fluid, *Phys. Rev. Lett.*, 92:235501-1-235501-4 (2004).
Petkus et al., Detection of FITC-Cortisol via Modulated Supraparticle Lighthouses, *Anal. Chem.*, 78:1405-1411 (2006).

(56) References Cited

OTHER PUBLICATIONS

Puig-de-Morales et al., Measurement of Cell Microrheology by Magnetic Twisting Cytometry with Frequency Domain Demodulation, *J. Appl. Physiol.*, 91:1152-1159 (2001).

Purcell et al., Life at Low Reynolds Number, *Am. J. Phys.*, 45:3-11 (1977).

Richards-Kortum et al., Quantitative Optical Spectroscopy for Tissue Diagnosis, *Annual Review of Physical Chemistry*, 47:555-606 (1996).

Rife et al., Design and Performance of GMR Sensors for the Detection of Magnetic Microbeads in Biosensors, *Sensors and Actuators A.*, 107:209-218 (2003).

Ross et al., Viscosity study of DNA. II. The effect of simple salt concentration on the viscosity of high molecular weight DNA and application of viscometry to the study of DNA isolated from T4 and T5 bacteriophage mutants, Biopolymers, 6(8):1005-18 (1968).

Sakoulas et al., Relationship of MIC and bactericidal activity to efficacy of vancomycin for treatment of methicillin-resistant *Staphylococcus aureus* bacteremia, J. Clin. Microbiol., 42(6):2398-402 (2004).

Sanghvi et al., Heterocyclic base modifications in nucleic acids and their applications in antisense oligonucleotides, Chapter 15 IN: Crooke et al. (eds.), *Antisense Research and Applications*, Boca Raton: CRC Press (1993).

Shankar et al., Experimental Determination of the Kinematic Viscosity of Glycerol-Water Mixtures, *Proc. R. Soc. Lond. A.*, 444:573-581 (1994).

Sheely, Glycerol viscosity tables, Industrial & Engineering Chem., 24(9):1060-4 (1932).

Shelton et al., Nonlinear Motion of Optically Torqued Nanorods, *Phys. Rev. E.*, 71:036204-1-036204-8 (2005).

Shen et al., In situ Detection of Single Micron-Sized Magnetic Beads using Magnetic Tunnel Junction Sensors, *Appl. Phys. Letts.*, 86:253901-1-253901-3 (2005).

Shine et al., The Rotation of a Suspended Axisymmetric Ellipsoid in a Magnetic Field, *Rheol. Acta*, 26:152-161 (1987).

Sinn et al., Asynchronous magnetic bead rotation (AMBR) biosensor in microfluidic droplets for rapid bacterial growth and susceptibility measurements, Lab Chip, 11(15):2604-11 (2011).

Sinn et al., Magnetically uniform and tunable Janus particles, Appl. Phys. Lett., 98:024101 (2011).

Spellberg et al., Trends in antimicrobial drug development: implications for the future, Clin. Infect. Dis., 38(9):1279-86 (2004).

Srivastava et al., Nanoliter viscometer for analyzing blood plasma and other liquid samples, Anal. Chem., 77(2):383-92 (2005).

Stober et al., Controlled Growth of Monodisperse Silica Spheres in the Micron Size Range, *J. Coll. Interface Sci.*, 26:62-69 (1968).

Su et al., A self-assembled monolayer-based piezoelectric immunosensor for rapid detection of *Escherichia coli* O157:H7, Biosens. Bioelectron., 19(6):563-74 (2004).

Talbot et al., Bad bugs need drugs: an update on the development pipeline from the Antimicrobial Availability Task Force of the Infectious Diseases Society of America, Clin. Infect. Dis., 42(5):657-68 (2006).

Tang et al., Molecular diagnostics of infectious diseases, Clin. Chem., 43(11):2021-38 (1997).

Taylor et al., Real-time molecular and cellular analysis: the new frontier of drug discovery, *Current Opinion in Biotechnology*, 12(1):75-81 (2001).

Tenover et al., The challenges of emerging infectious diseases. Development and spread of multiply-resistant bacterial pathogens, JAMA, 275(4):300-4 (1996).

Tiemersma et al., Methicillin-resistant *Staphylococcus aureus* in Europe, 1999-2002, Emerg. Infect. dis., 10(9):1627-34 (2004).

Tokarev et al., Magnetic rotational spectroscopy with nanorods to probe time-dependent rheology of microdroplets, Langmuir, 28(26):10064-71 (2012).

Tsortos et al., The intrinsic viscosity of linear DNA, Biopolymers, 95:824 (2011).

Valasek et al., The power of real-time PCR, Adv. Physiol. Educ., 29(3):151-9 (2005).

Valberg et al., Magnetic particle motions within living cells. Physical theory and techniques, *Biophysical Journal*, 52(4):537-550 (1987).

Van Oorschot et al., Forensic trace DNA: a review, Investig. Genet., 1(1):14 (2010).

Varshney, Interdigitated array microelectrodes based impedance biosensors for detection of bacterial cells, Biosens. Bioelectron., 24(10):2951-60 (2009).

Verbridge et al., High Quality Factor Resonance at Room Temperature with Nanostrings Under High Tensile Stress, *J. Appl. Phys.*, 99:124304-1-124304-8 (2006).

Vignola et al., Effect of Viscous Loss on Mechanical Resonators Designed for Mass Detection, *Appl. Phys. Lett.*, 88:041921-1-041921-3 (2006).

Wagnieres et al., In vivo fluorescence spectroscopy and imaging for oncological applications, *Photochemistry and Photobiology*, 68(5):603-632 (1998).

Waigh, Microrheology of Complex Fluids, *Rep. Prog. Phys.*, 68:685-742 (2005).

Witte et al., Changing pattern of antibiotic resistance in methicillin-resistant *Staphylococcus aureus* from German hospitals, Infect. Control Hosp. Epidemiol., 22(11):683-6 (2001).

Witte, Antibiotic resistance in gram-positive bacteria: epidemiological aspects, J. Antimicrob. Chemother., 44 Suppl A:1-9 (1999).

Yamazaki et al., Three-Dimensional Analysis of Swimming Properties of a Spiral-Type Magnetic Micro-Machine, *Sensors and Actuators A.*, 105:103-108 (2003).

Yang et al., Interdigitated Array microelectrode-based electrochemical impedance immunosensor for detection of *Escherichia coli* O157:H7, Anal. Chem., 76(4):1107-13 (2004).

Zhao et al., A Rapid Bioassay for Single Bacterial Cell Quantitation Using Bioconjugated Nanoparticles, *PNAS*, 101:15027-15032 (2004).

Curtin, et al. "Utilising μ-PIV and pressure measurements to determine the viscosity of a DNA solution in a microchannel," Experimental Thermal and Fluid Science 30:843-852 (2006).

Laesecke, et al. "Viscosity measurements of DNA solutions with and without condensing agents," Biorheology 52:15-28 (2014).

FIG. 5A
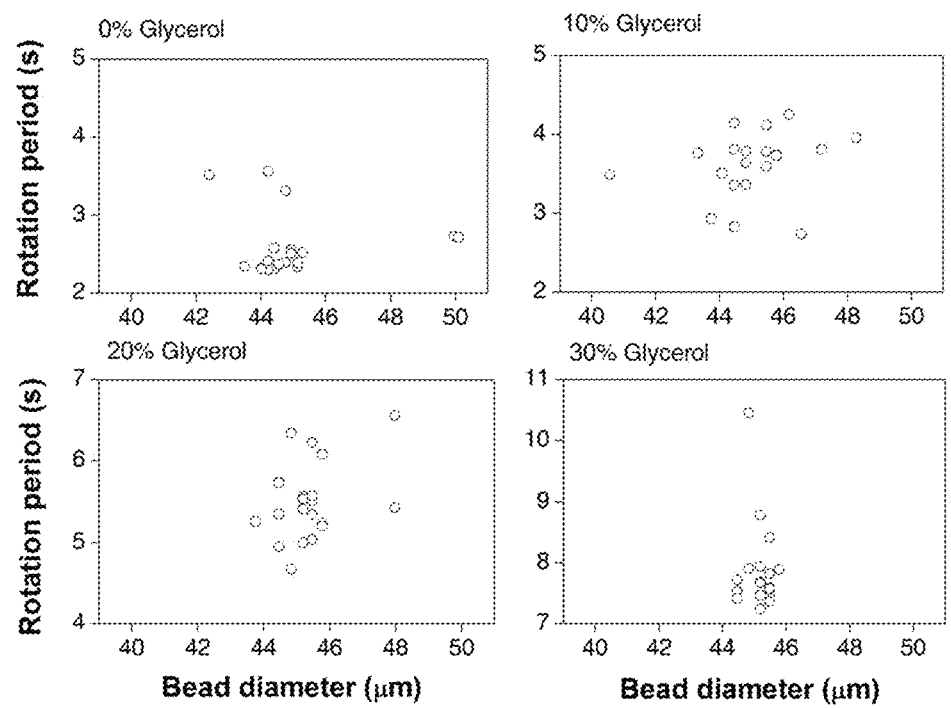
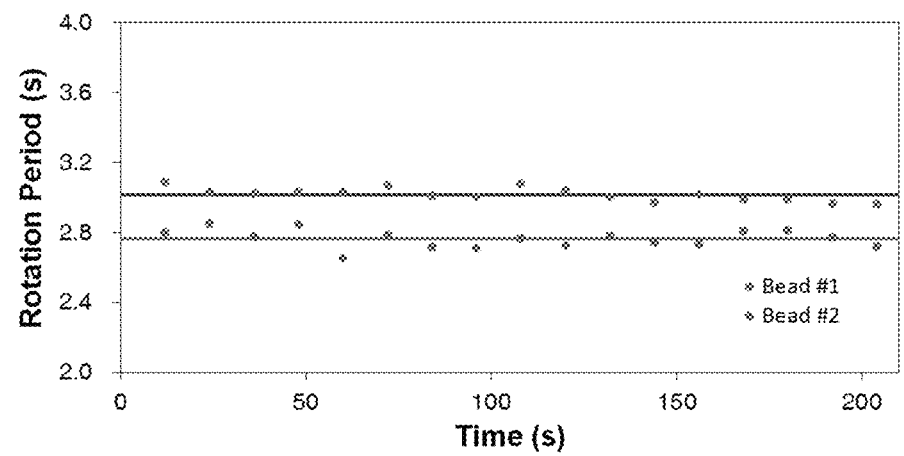
FIG. 5B

FIG. 6A
FIG. 6B
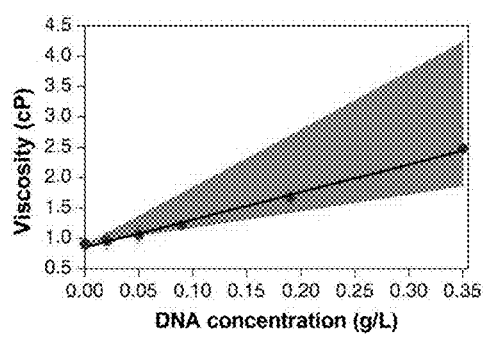
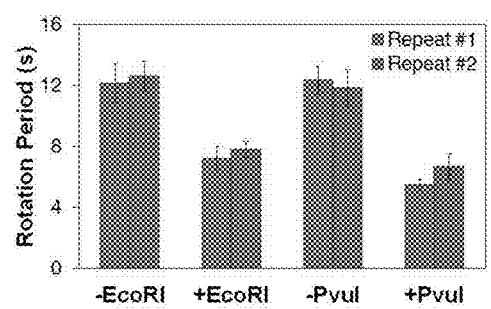
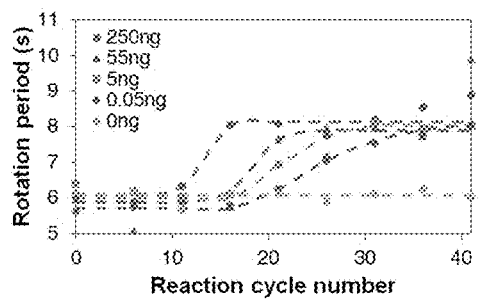
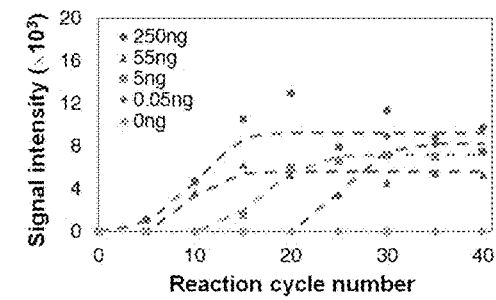
FIG. 6C
FIG. 6D

ASYNCHRONOUS MAGNETIC BEAD ROTATION (AMBR) MICROVISCOMETER FOR ANALYSIS OF ANALYTES

CROSS REFERENCE TO RELATED APPLICATIONS

This application claims the priority benefit under 35 U.S.C. § 119(e) of U.S. Provisional Patent Application No. 61/899,660, filed Nov. 4, 2013, the disclosure of which is incorporated herein by reference in its entirety.

STATEMENT OF GOVERNMENT INTEREST

This invention was made with government support under federal grants EB006789 and HG005077 awarded by the National Institutes of Health. The Government has certain rights in the invention.

SEQUENCE LISTING

This application contains, as a separate part of the disclosure, a Sequence Listing in computer-readable form (filename: 48118A_SeqListing.txt; created: Nov. 4, 2014; 730 bytes—ASCII text file) which is incorporated by reference in its entirety.

FIELD OF THE INVENTION

The present disclosure is directed to a microviscometer based on asynchronous magnetic bead rotation (AMBR) and used for analyte detection.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Sensitive and cost-effective DNA detection methods have a wide range of applications, from clinical diagnostics and drug development to the food industry and forensic sciences [Tang et al., Clin. Chem. 43(11): 2021-2038 (1997); Valasek et al., Adv Physiol Educ 29(3): 151-159 (2005); Mandal et al., Am. J. Food Technol 6: 87-102 (2011); van Oorschot et al., Investig genet 1(1), 14 (2010)]. In medical diagnostics, especially for infectious diseases, DNA detection technology such as quantitative polymerase chain reaction (qPCR), restriction fragment length polymorphism (RFLP) and ligation detection reaction (LDR) are crucial diagnostic tools [Landegren et al., Science 242(4876): 229-237 (1998); Kubista et al., Mol Aspects Med 27(2-3), 95-125 (2006); Handal et al., Expert Review of Molecular Diagnostics 6(1), 29-38 (2006)]. Fluorescence has been used almost exclusively as the DNA detection method in these tools due to its simplicity and high sensitivity [Kubista et al., Mol Aspects Med 27(2-3), 95-125 (2006); Handal et al., Expert Review of Molecular Diagnostics 6(1), 29-38 (2006)]. Recently, numerous efforts have been made to seek more cost-effective DNA detection technologies, notably for use in the developing world, yet none of them achieve the same sensitivity and applicability as fluorescence-based methods [Li et al., PLoS ONE 6(12): e29224 (2011); Diakite et al., Lab Chip 12(22): 4738-4747 (2012); Leslie et al., J. Am. Chem. Soc. 134(12): 5689-5696 (2012)].

Another approach to detect and quantify DNA in diagnostic reactions is to measure the solution viscosity [Livak-Dahl et al., Lab on a Chip 13(2): 297 (2013); Srivastava et al., Anal. Chem. 77(2): 383-392 (2005)]. The viscosity of a double-stranded DNA (dsDNA) solution at a known temperature depends on the mass concentration and the average length of the DNA strands. The solution viscosity can indicate DNA concentration and/or length [Huggins J. Am. Chem. Soc. 64(11): 2716-2718 (1942); Ross et al., Biopolymers 6(8): 1005-1018 (1968); Tsortos et al., Biopolymers 95(12), 824-832 (2011)]. In restriction digestion reactions the solution viscosity decreases as longer DNA strands are cut into shorter pieces. Alternatively, in PCR, the solution viscosity increases as the length of the DNA increases, through polymerization of the target sequence.

SUMMARY OF THE INVENTION

Disclosed herein is a microviscometer that is based on asynchronous magnetic bead rotation (AMBR) and used for analyte detection. AMBR detection monitors the rotational motion of a free-floating magnetic bead placed in a rotating magnetic field and uses changes in this motion to infer physical properties of the surrounding solution. When the rotation rate of the external field exceeds a critical value, the bead rotates at a speed different from that of the external field. The rate of this asynchronous rotation is viscosity dependent. Readily available paramagnetic microbeads can thus be used for measuring changes in analyte concentrations or average lengths of specific analytes, such as, without limitation, DNA.

Accordingly, in one aspect the disclosure provides a method of detecting a change in state of an analyte in a sample comprising (a) contacting the sample with a magnetic particle; (b) measuring a first instantaneous non-linear rotation rate of the magnetic particle in the sample at a first time; and (c) measuring a second instantaneous non-linear rotation rate of the magnetic particle in the sample at a second time Y; wherein a difference between the first instantaneous rotation rate relative to the second instantaneous rotation rate indicates the change in state of the analyte in the sample.

In some embodiments, the change in state is a physical change in state. In further embodiments, the physical change in state further comprises a change in temperature of the sample comprising the analyte. In related embodiments, the analyte is water or a population of cells.

In additional embodiments, the change in state is a chemical change in state. In related embodiments, the analyte is a monomer of a biopolymer. In further embodiments, the analyte is selected from the group consisting of a cell, a nucleic acid, a protein, a carbohydrate, a lipid, and an amino acid. In still further embodiments, the chemical change is catalyzed by an enzyme. The enzyme, in some embodiments, is selected from the group consisting of a polymerase, a nuclease, a hydrolase, a lyase, an oxidase, a peptidase, and a ligase.

In further embodiments, the chemical change is selected from the group consisting of nucleic acid synthesis, protein synthesis, nucleic acid hydrolysis, nucleic acid ligation, and protein hydrolysis. In some embodiments, the nucleic acid synthesis is by polymerase chain reaction (PCR). In further embodiments, the protein synthesis is by in vitro translation. In additional embodiments, the protein synthesis occurs in a cell. In some embodiments, the nucleic acid hydrolysis is catalyzed by a type I or a type II restriction endonuclease.

The chemical change, in some embodiments, is formation or loss of a nucleic acid hybrid, a blood clot, or a ligand-receptor interaction, a nucleic acid-protein interaction, a protein-lipid interaction, a protein-carbohydrate interaction, an antibody-antigen interaction. In further embodiments, the chemical change occurs in a supercooled liquid or in an electric battery fluid while the battery is charging.

In various embodiments, the difference between the first rotation rate relative to the second rotation rate indicates a change in concentration of analyte in the sample.

In various embodiments, the difference between the first rotation rate relative to the second rotation rate indicates a change in average length of analyte in the sample.

In further embodiments of the disclosure, the difference between the first rotation rate relative to the second rotation rate is measured in real time.

BRIEF DESCRIPTION OF THE DRAWINGS

FIG. 1 depicts the Asynchronous Magnetic Bead Rotation (AMBR) microviscometer.

FIG. 3 shows calibration curves of 45 µm bead at different driving frequencies.

FIG. 4 shows calibration curves at 100 Hz using beads of different sizes.

FIG. 5 shows the reproducibility of AMBR viscosity measurements at 100 Hz driving frequency. FIG. 5(a) Rotation period measurement of 20 independent beads in the same solution plotted against the optically measured bead size of each bead. FIG. 5(b) The rotation periods of two examples of 45 µm beads observed over time in the same solution. The rotation periods are calculated over a 12 s period and plotted in the graph. The average values are for 17 sequential observations.

FIG. 6 shows DNA measurements using AMBR microviscometer. FIG. 6(a) Viscosities of lambda DNA EcoRI digested DNA at different concentrations, as measured by AMBR microviscometer. The dark area indicates the expected range of the viscosity calculated theoretically, assuming that only the longest (top range) or only the shortest (bottom range) DNA fragment size are present. Error bars represent standard deviation among 10 beads in one measurement. FIG. 6(b) Measurement of bead rotation period of pre- and post-digestion samples of lambda phage DNA by AMBR microviscometer. The field driving frequency is 150 Hz. The error bars show the standard deviation among 10 beads in each measurement. FIG. 6(c) Measurement of viscosity by bead rotation period in PCR reactions sampled every 5 cycles, starting from the 6th cycle. PCR reactions with initial DNA amounts of 0 ng, 0.05 ng, 5 ng, 55 ng, and 250 ng are shown. The reaction volumes are 50 µL each. The field driving frequency is 150 Hz, and the PCR product size is 4500 bp. Each point represents the mean value, observing ten beads. FIG. 6(d) Fluorescent signal intensities of the PCR product (4500 bp band) observed on a electrophoresis gel for the same samples measured in FIG. 6(c).

DETAILED DESCRIPTION OF THE INVENTION

Figure 1A:
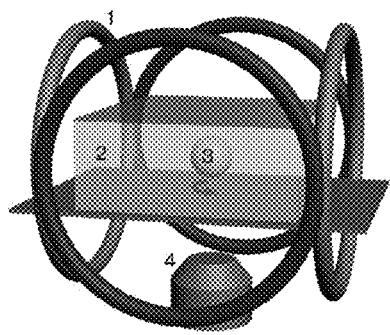
FIG. 1(a) A schematic experimental set-up of an AMBR microviscometer. 1: perpendicular Helmholtz coils for rotating field generation; 2: liquid to be measured; 3: magnetic bead; 4: inverted microscope objective.

Described herein are methods for analysis of one or more analytes using magnetic particles. In particular, described herein are asynchronous magnetic bead rotation (AMBR) methods for analysis of analytes. AMBR is additionally described in U.S. Pat. No. 8,846,331, incorporated herein by reference in its entirety. The methods of the disclosure are based on the use of a magnetic particle, which magnetic particle is free in the sample volume and is not tethered to the analyte of interest. As a result of a change in state of the analyte, the viscosity of the sample is varied. Such a variance in the viscosity is detectable by the magnetic particle and the use of AMBR technology, and is correlated with the change in state. The change in state can be translated to, for example and without limitation, the concentration of the analyte in the sample and/or the average length of an analyte. Moreover, the present techniques are able to detect microviscosity changes which correlate to small scale changes in the analyte, such as small scale changes in the length or concentration of the analyte. Moreover still, these microviscosity changes that can be measured may be used in various other physical state change and chemical change applications. For example, viscosity changes, measured through an AMBR technology can be used to detect deterioration of chemicals in a solution, e.g. deterioration of engine oils over time, olive oils, etc. Plus these chemical changes may be measured at scales heretofore un-attainable through conventional means, not without expensive equipment such as molecular imaging techniques, and the like.

In a specific aspect, the present disclosure provides a method of detecting amplification of a nucleic acid (e.g., DNA) in a sample in real-time. In such an aspect, the change in viscosity that occurs in the sample via the polymerization of DNA is detectable by the magnetic particle using the methods described herein.

As can be seen, generally speaking, the present techniques may be used to determine any number of small scale physical state changes and chemical changes, in solution, so long as those changes result in and correlate to small-scale, e.g., microviscometric. changes in the solution, i.e., viscosity changes detectable through the techniques described herein.

The advantages of using the methods provided by the disclosure center on the ability of the AMBR microviscometer to detect very small changes in the viscosity of a sample. Further, such small changes in viscosity are detectable in small sample volumes. It was unexpected that such small changes in viscosity (e.g., the changes in viscosity generated in a sample in which qPCR is being performed) could be detected using the AMBR technique. In view of such an ability of the AMBR technique, however, new applications are made available. For example, and without limitation, use of the methods provided herein eliminate the need for a label (such as a fluorescent label) and also allow for rapid quantification of an analyte in real-time.

It is noted here that, as used in this specification and the appended claims, the singular forms "a," "an," and "the" include plural reference unless the context clearly dictates otherwise.

Asynchronous Magnetic Bead Rotation (AMBR)

Typically, in AMBR, a magnetic particle (e.g., a bead) is exposed to a driving rotating magnetic field that is rotating above a critical frequency so that the rotational rate of the magnetic particle is sensitized to changes in the shape or size of the particle including object bound to the particle. In some cases (e.g., particularly with ferromagnetic beads) at low driving rates the magnetic bead rotates synchronously with the driving magnetic field, referred to as the synchronous mode. When the magnetic particle rotates at a rate that is slower than the driving rate, the system may be referred to as operating in the asynchronous mode. In contrast to the synchronous mode, in the asynchronous mode the rate of rotation of the magnetic particle slows as viscosity of the solution comprising the analyte increases. While the magnetic particles remain in the synchronous mode, changes in viscosity do not slow the rotation of the magnetic particle.

The magnetic particles that may be used for AMBR are, in various embodiments, paramagnetic, superparamagnetic, or ferromagnetic. Although the various examples described herein refer to analytes that are DNA, other analytes may be detected, including but not limited to molecules (proteins, carbohydrates, etc.), nucleotides, cells, and the like. If the analyte is a cell, such as a prokaryotic or eukaryotic cell or cells (e.g., bacterial, cancer cells, etc.), the rate of rotation of the magnetic particle in the asynchronous rotation mode may depend upon the concentration or aggregation of the cells in a solution. Changes in the cell number or changes in the aggregation of the cells will alter the rotational rate of the magnetic particles. Thus, by monitoring the rate of rotation of the magnetic bead or beads in the asynchronous mode, it is possible to detect and monitor changes in viscosity of the solution comprising the analyte.

Currently, AMBR systems may monitor the rotation of magnetic particles under the driving rotating magnetic field to detect the asynchronous rate of rotation. The rate of rotation is typically monitored using a laser (e.g., focusing laser or coherent light source), a microscope, camera, and typically software to help visualize and detect the rate of rotation. Devices, systems and methods performing AMBR are described in, e.g., U.S. Pat. No. 8,846,331, incorporated herein by reference, in relevant part.

AMBR devices use magnetic beads that may rotate asynchronously when a driving magnetic field used to rotate the magnetic beads exceeds a critical frequency. Above this critical frequency, the particle's rotation is asynchronous with the external field, thus the particle is in an asynchronous condition. In some of the variations described herein, the magnetic beads are clustered so that the AMBR technique may be applied by rotating the entire cluster (or in some variations multiple clusters) of magnetic particles in the asynchronous mode. Changes in this asynchronous rotational rate of the entire cluster of particles may be used to detect changes in viscosity of a solution. Furthermore, measurement of a cluster's rotation can be performed with any of the AMBR devices described in U.S. Pat. No. 8,846,331 using low-cost and readily available electronic components, e.g. diodes and photodiodes, allowing for broad applicability. Rather than only being able to measure changes in viscosity, the AMBR methods described herein are powerful in that they are able to correlate small changes in viscosity with a quantification of the concentration of an analyte and/or the average length of an analyte such as a nucleic acid.

Relative to previous understanding of AMBR, the methods of the disclosure advantageously work in small sample volumes. In various embodiments, methods for detecting a change in state of an analyte in a sample are performed in a volume of from about 1 picoliter (pL) to about 1 milliliter (mL). In further embodiments, the methods are performed in a volume of from about 1 pL to about 100 microliters (0), or from about 50 pL to about 100 μl, or from about 100 pL to about 100 μl, or from about 500 pL to about 100 μl, or from about 1 μl to about 100 μl, or from about 1 μl to about 90 μl, or from about 1 μl to about 80 μl, or from about 1 μl to about 70 μl, or from about 1 μl to about 60 μl, or from about 1 μl to about 50 μl, or from about 1 μl to about 40 μl, or from about 1 μl to about 30 μl, or from about 1 μl to about 20 μl, or from about 1 μl to about 10 μl, or from about 1 μl to about 5 μl, or from about 10 μl to about 100 μl, or from about 10 μl to about 90 μl, or from about 10 μl to about 80 μl, or from about 10 μl to about 70 μl, or from about 10 μl to about 60 μl, or from about 10 μl to about 50 μl, or from about 10 μl to about 40 μl, or from about 10 μl to about 30 μl, or from about 10 μl to about 20 μl, or from about 20 μl to about 100 μl, or from about 20 μl to about 90 μl, or from about 20 μl to about 80 μl, or from about 20 μl to about 70 μl, or from about 20 μl to about 60 μl, or from about 20 μl to about 50 μl, or from about 20 μl to about 40 μl, or from about 20 μl to about 30 μl, or from about 30 μl to about 100 μl, or from about 30 μl to about 90 μl, or from about 30 μl to about 80 μl, or from about 30 μl to about 70 μl, or from about 30 μl to about 60 μl, or from about 30 μl to about 50 μl, or from about 30 μl to about 40 μl, or from about 40 μl to about 100 μl, or from about 40 μl to about 90 μl, or from about 40 μl to about 80 μl, or from about 40 μl to about 70 μl, or from about 40 μl to about 60 μl, or from about 40 μl to about 50 μl, or from about 50 μl to about 100 μl, or from about 50 μl to about 90 μl, or from about 50 μl to about 80 μl, or from about 50 μl to about 70 μl, or from about 50 μl to about 60 μl, or from about 60 μl to about 100 pi, or from about 60 μl to about 90 μl, or from about 60 μl to about 80 μl, or from about 60 μl to about 70 μl, or from about 70 μl to about 100 μl, or from about 70 μl to about 90 μl, or from about 70 μl to about 80 μl, or from about 80 μl to about 100 μl, or from about 80 μl to about 90 μl, or from about 90 μl to about 100 μl. In still further embodiments, the methods are performed in a volume that is or is at least 1 μl, is or is at least 2 μl, is or is at least 3 μl, is or is at least 4 μl, is or is at least 5 μl, is or is at least 6 µl, is or is at least 7 µl, is or is at least 8 µl, is or is at least 9 µl, is or is at least 10 µl, is or is at least 11 µl, is or is at least 12 µl, is or is at least 13 µl, is or is at least 14 µl, is or is at least 15 µl, is or is at least 16 µl, is or is at least 17 µl, is or is at least 18 µl, is or is at least 19 µl, is or is at least 20 µl, is or is at least 21 µl, is or is at least 22 µl, is or is at least 23 µl, is or is at least 24 µl, is or is at least 25 µl, is or is at least 26 µl, is or is at least 27 µl, is or is at least 28 µl, is or is at least 29 µl, is or is at least 30 µl, is or is at least 31 µl, is or is at least 32 µl, is or is at least 33 µl, is or is at least 34 µl, is or is at least 35 µl, is or is at least 36 µl, is or is at least 37 µl, is or is at least 38 µl, is or is at least 39 µl, is or is at least 40 µl, is or is at least 41 µl, is or is at least 42 µl, is or is at least 43 µl, is or is at least 44 µl, is or is at least 45 µl, is or is at least 46 µl, is or is at least 47 µl, is or is at least 48 µl, is or is at least 49 µl, is or is at least 50 µl, is or is at least 51 µl, is or is at least 52 µl, is or is at least 53 µl, is or is at least 54 µl, is or is at least 55 µl, is or is at least 56 µl, is or is at least 57 µl, is or is at least 58 µl, is or is at least 59 µl, is or is at least 60 µl, is or is at least 61 µl, is or is at least 62 µl, is or is at least 63 µl, is or is at least 64 µl, is or is at least 65 µl, is or is at least 66 µl, is or is at least 67 µl, is or is at least 68 µl, is or is at least 69 µl, is or is at least 70 µl, is or is at least 71 µl, is or is at least 72 µl, is or is at least 73 µl, is or is at least 74 µl, is or is at least 75 µl, is or is at least 76 µl, is or is at least 77 µl, is or is at least 78 µl, is or is at least 79 µl, is or is at least 80 µl, is or is at least 81 µl, is or is at least 82 µl, is or is at least 83 µl, is or is at least 84 µl, is or is at least 85 µl, is or is at least 86 µl, is or is at least 87 µl, is or is at least 88 µl, is or is at least 89 µl, is or is at least 90 µl, is or is at least 91 µl, is or is at least 92 µl, is or is at least 93 µl, is or is at least 94 µl, is or is at least 95 µl, is or is at least 96 µl, is or is at least 97 µl, is or is at least 98 µl, is or is at least 99 µl, or is or is at least 100 µl or more.

As disclosed herein, and also relative to previous understanding of AMBR, the methods provided by the disclosure are capable of detecting small changes in viscosity in a sample. Thus, in various embodiments of the methods, a change in viscosity that is from about 0.01 centipoise (cP) to about 10 cP is detected. In some embodiments, the change in viscosity that is detected is from about 0.01 cP to about 9 cP, or from about 0.01 cP to about 8 cP, or from about 0.01 cP to about 7 cP, or from about 0.01 cP to about 6 cP, or from about 0.01 cP to about 5 cP, or from about 0.01 cP to about 4 cP, or from about 0.01 cP to about 3 cP, or from about 0.01 cP to about 2 cP, or from about 0.01 cP to about 1 cP, or from about 0.01 cP to about 0.5 cP, or from about 0.1 centipoise (cP) to about 10 cP, or from about 0.1 cP to about 9 cP, or from about 0.1 cP to about 8 cP, or from about 0.1 cP to about 7 cP, or from about 0.1 cP to about 6 cP, or from about 0.1 cP to about 5 cP, or from about 0.1 cP to about 4 cP, or from about 0.1 cP to about 3 cP, or from about 0.1 cP to about 2 cP, or from about 0.1 cP to about 1 cP, or from about 0.1 cP to about 0.5 cP, or from about 0.5 cP to about 10 cP, or from about 0.5 cP to about 9 cP, or from about 0.5 cP to about 8 cP, or from about 0.5 cP to about 7 cP, or from about 0.5 cP to about 6 cP, or from about 0.5 cP to about 5 cP, or from about 0.5 cP to about 4 cP, or from about 0.5 cP to about 3 cP, or from about 0.5 cP to about 2 cP, or from about 0.5 cP to about 1 cP, or from about 1 cP to about 10 cP, or from about 1 cP to about 9 cP, or from about 1 cP to about 8 cP, or from about 1 cP to about 7 cP, or from about 1 cP to about 6 cP, or from about 1 cP to about 5 cP, or from about 1 cP to about 4 cP, or from about 1 cP to about 3 cP, or from about 1 cP to about 2 cP, or from about 1 cP to about 1.5 cP, or from about 2 cP to about 10 cP, or from about 2 cP to about 9 cP, or from about 2 cP to about 8 cP, or from about 2 cP to about 7 cP, or from about 2 cP to about 6 cP, or from about 2 cP to about 5 cP, or from about 2 cP to about 4 cP, or from about 2 cP to about 3 cP, or from about 3 cP to about 10 cP, or from about 3 cP to about 9 cP, or from about 3 cP to about 8 cP, or from about 3 cP to about 7 cP, or from about 3 cP to about 6 cP, or from about 3 cP to about 5 cP, or from about 3 cP to about 4 cP, or from about 4 cP to about 10 cP, or from about 4 cP to about 9 cP, or from about 4 cP to about 8 cP, or from about 4 cP to about 7 cP, or from about 4 cP to about 6 cP, or from about 4 cP to about 5 cP, or from about 5 cP to about 10 cP, or from about 5 cP to about 9 cP, or from about 5 cP to about 8 cP, or from about 5 cP to about 7 cP, or from about 5 cP to about 6 cP, or from about 6 cP to about 10 cP, or from about 6 cP to about 9 cP, or from about 6 cP to about 8 cP, or from about 6 cP to about 7 cP, or from about 7 cP to about 10 cP, or from about 7 cP to about 9 cP, or from about 7 cP to about 8 cP, or from about 8 cP to about 10 cP, or from about 8 cP to about 9 cP, or from about 9 cP to about 10 cP. In further embodiments, the methods of the disclosure are capable of detecting a change in viscosity in a sample that is or is at least 0.01 cP, is or is at least 0.02 cP, is or is at least 0.03 cP, is or is at least 0.04 cP, is or is at least 0.05 cP, is or is at least 0.06 cP, is or is at least 0.07 cP, is or is at least 0.08 cP, is or is at least 0.09 cP, is or is at least 0.1 cP, is or is at least 0.11 cP, is or is at least 0.12 cP, is or is at least 0.13 cP, is or is at least 0.14 cP, is or is at least 0.15 cP, is or is at least 0.16 cP, is or is at least 0.17 cP, is or is at least 0.18 cP, is or is at least 0.19 cP, is or is at least 0.2 cP, is or is at least 0.21 cP, is or is at least 0.22 cP, is or is at least 0.23 cP, is or is at least 0.24 cP, is or is at least 0.25 cP, is or is at least 0.26 cP, is or is at least 0.27 cP, is or is at least 0.28 cP, is or is at least 0.29 cP, is or is at least 0.3 cP, is or is at least 0.31 cP, is or is at least 0.32 cP, is or is at least 0.33 cP, is or is at least 0.34 cP, is or is at least 0.35 cP, is or is at least 0.36 cP, is or is at least 0.37 cP, is or is at least 0.38 cP, is or is at least 0.39 cP, is or is at least 0.4 cP, is or is at least 0.41 cP, is or is at least 0.42 cP, is or is at least 0.43 cP, is or is at least 0.44 cP, is or is at least 0.45 cP, is or is at least 0.46 cP, is or is at least 0.47 cP, is or is at least 0.48 cP, is or is at least 0.49 cP, is or is at least 0.5 cP, is or is at least 0.51 cP, is or is at least 0.52 cP, is or is at least 0.53 cP, is or is at least 0.54 cP, is or is at least 0.55 cP, is or is at least 0.56 cP, is or is at least 0.57 cP, is or is at least 0.58 cP, is or is at least 0.59 cP, is or is at least 0.6 cP, is or is at least 0.61 cP, is or is at least 0.62 cP, is or is at least 0.63 cP, is or is at least 0.64 cP, is or is at least 0.65 cP, is or is at least 0.66 cP, is or is at least 0.67 cP, is or is at least 0.68 cP, is or is at least 0.69 cP, is or is at least 0.7 cP, is or is at least 0.71 cP, is or is at least 0.72 cP, is or is at least 0.73 cP, is or is at least 0.74 cP, is or is at least 0.75 cP, is or is at least 0.76 cP, is or is at least 0.77 cP, is or is at least 0.78 cP, is or is at least 0.79 cP, is or is at least 0.8 cP, is or is at least 0.81 cP, is or is at least 0.82 cP, is or is at least 0.83 cP, is or is at least 0.84 cP, is or is at least 0.85 cP, is or is at least 0.86 cP, is or is at least 0.87 cP, is or is at least 0.88 cP, is or is at least 0.89 cP, is or is at least 0.9 cP, is or is at least 0.91 cP, is or is at least 0.92 cP, is or is at least 0.93 cP, is or is at least 0.94 cP, is or is at least 0.95 cP, is or is at least 0.96 cP, is or is at least 0.97 cP, is or is at least 0.98 cP, is or is at least 0.99 cP, is or is at least 1 cP, is or is at least 1.1 cP, is or is at least 1.2 cP, is or is at least 1.3 cP, is or is at least 1.4 cP, is or is at least 1.5 cP, is or is at least 1.6 cP, is or is at least 1.7 cP, is or is at least 1.8 cP, is or is at least 1.9 cP, is or is at least 2 cP, is or is at least 2.1 cP, is or is at least 2.2 cP, is or is at least 2.3 cP, is or is at least 2.4 cP, is or is at least 2.5 cP, is or is at least 2.6 cP, is or is at least 2.7 cP, is or is at least 2.8 cP, is or is at least 2.9 cP, is or is at least 3 cP, is or is at least 3.1 cP, is or is at least 3.2 cP, is or is at least 3.3 cP, is or is at least 3.4 cP, is or is at least 3.5 cP, is or is at least 3.6 cP, is or is at least 3.7 cP, is or is at least 3.8 cP, is or is at least 3.9 cP, is or is at least 4 cP, is or is at least 4.1 cP, is or is at least 4.2 cP, is or is at least 4.3 cP, is or is at least 4.4 cP, is or is at least 4.5 cP, is or is at least 4.6 cP, is or is at least 4.7 cP, is or is at least 4.8 cP, is or is at least 4.9 cP, is or is at least 5 cP, is or is at least 5.1 cP, is or is at least 5.2 cP, is or is at least 5.3 cP, is or is at least 5.4 cP, is or is at least 5.5 cP, is or is at least 5.6 cP, is or is at least 5.7 cP, is or is at least 5.8 cP, is or is at least 5.9 cP, is or is at least 6 cP, is or is at least 6.1 cP, is or is at least 6.2 cP, is or is at least 6.3 cP, is or is at least 6.4 cP, is or is at least 6.5 cP, is or is at least 6.6 cP, is or is at least 6.7 cP, is or is at least 6.8 cP, is or is at least 6.9 cP, is or is at least 7 cP, is or is at least 7.1 cP, is or is at least 7.2 cP, is or is at least 7.3 cP, is or is at least 7.4 cP, is or is at least 7.5 cP, is or is at least 7.6 cP, is or is at least 7.7 cP, is or is at least 7.8 cP, is or is at least 7.9 cP, is or is at least 8 cP, is or is at least 8.1 cP, is or is at least 8.2 cP, is or is at least 8.3 cP, is or is at least 8.4 cP, is or is at least 8.5 cP, is or is at least 8.6 cP, is or is at least 8.7 cP, is or is at least 8.8 cP, is or is at least 8.9 cP, is or is at least 9 cP, is or is at least 9.1 cP, is or is at least 9.2 cP, is or is at least 9.3 cP, is or is at least 9.4 cP, is or is at least 9.5 cP, is or is at least 9.6 cP, is or is at least 9.7 cP, is or is at least 9.8 cP, is or is at least 9.9 cP, or is or is at least 10 cP.

In addition, changes in the concentration of an analyte over time are detectable using the methods of the disclosure. Such quantification over time allows for use of the techniques in monitoring, for example, nucleic acid synthesis, protein synthesis, nucleic acid hydrolysis, nucleic acid ligation, and protein hydrolysis.

Analytes

The methods provided herein allow for the quantification of an analyte in a sample. The quantification, in various aspects, involves quantitating a concentration of the analyte and/or quantifying an average size of the analyte. Any analyte that, when present, changes the viscosity of the sample through a change in state is amenable to the methods disclosed herein. The "change in state" as used herein takes on its ordinary meaning in the art. Thus, the methods disclosed herein allow for the detection and analysis of analytes undergoing both a physical change in state as well as a chemical change in state. In some embodiments, the methods herein are used to detect both a physical change in state and a chemical change in state in the same reaction.

In general, changes in state that are detectable by the methods of the disclosure include, without limitation, a polymerization reaction, a chain-cutting reaction (e.g., degrading polymers to make them shorter), a gelation reaction, growth of a cell population, a colloidal suspension (e.g., paints), or an age sensor (e.g., age of oil in a car).

Analytes contemplated by the disclosure for use according to the methods include, but are not limited to, a cell, a nucleic acid, a protein, a carbohydrate, a lipid, an amino acid, and derivatives thereof (e.g., nucleoproteins, glycosylated proteins, phospholipids). Additional analytes contemplated herein include, without limitation, a gel, a buffer, pulp. milk, and yogurt.

Cell

In some aspects, the present disclosure provides methods for detecting the presence of, and/or the aggregation of, cells. In various embodiments, the cell is a prokaryotic cell or the cell is a eukaryotic cell. In further embodiments, the cell is a cancer cell. Thus, in one embodiment the concentration of cells over time in a culture is quantified using an AMBR microviscometer technique as described herein. In another embodiment, the aggregation of cells in a sample (e.g., due to blood clotting) is detected using an AMBR microviscometer technique as described herein. In yet other embodiments, the interaction of dissimilar cell types is assessed or exploited, such as the interaction of a pathogenic (or non-pathogenic) bacterial cell and a eukaryotic cell.

Nucleic Acid

Nucleic acids contemplated by the present disclosure include DNA, RNA, modified forms and combinations thereof. In some embodiments, the DNA is double-stranded, and in further embodiments the DNA is single-stranded. In further aspects, the methods of the disclosure utilize RNA, and in some embodiments the RNA is double-stranded RNA. The term "RNA" includes duplexes of two separate strands, as well as single-stranded structures. Single-stranded RNA also includes RNA with secondary structure.

An oligomer of a nucleic acid is understood in the art to comprise individually polymerized nucleotide subunits and is referred to as an "oligonucleotide." The term "nucleotide" or its plural as used herein is interchangeable with modified forms as discussed herein and otherwise known in the art. In certain instances, the art uses the term "nucleobase" which embraces naturally occurring nucleotides, and non-naturally occurring nucleotides which include modified nucleotides. Thus, nucleotide or nucleobase includes the naturally occurring nucleosides and nucleotides containing any of adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety or in relevant part, as would be apparent from context). In various aspects, nucleic acid oligomers also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

In some aspects, methods of the disclosure provide the ability to determine the average length of a nucleic acid oligomer in a sample. In various embodiments, the length of a nucleic acid oligomer that is detectable using the methods disclosed herein is from about 20 to about 5000 nucleotides in length. Methods are also contemplated wherein the nucleic acid oligomer is about 20 to about 2000 nucleotides in length, about 20 to about 1000 nucleotides in length, about 20 to about 500 nucleotides in length, about 20 to about 400 nucleotides in length, about 20 to about 300 nucleotides in length about 20 to about 200 nucleotides in length, about 20 to about 100 nucleotides in length, about 20 to about 50 nucleotides in length, about 50 to about 4000 nucleotides in length, about 50 to about 3000 nucleotides in length, about 50 to about 2000 nucleotides in length, about 50 to about 1500 nucleotides in length, about 50 to about 1000 nucleotides in length, about 50 to about 800 nucleotides in length, about 50 to about 600, about 50 to about 500 nucleotides in length, about 50 to about 400, about 50 to about 300 nucleotides in length, about 50 to about 200 nucleotides in length, about 50 to about 100 nucleotides in length, and all nucleic acid oligomers intermediate in length of the sizes specifically disclosed. Accordingly, nucleic acid oligomers of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, or more nucleotides in length are contemplated as being detectable using the methods of the disclosure.

Protein/Amino Acid

As used herein a "protein" refers to a polymer comprised of amino acid residues and may also be referred to as a "polypeptide" in the art. Consistent with the understanding in the art, "protein" can also refer to the association (covalent or non-covalent) of distinct "polypeptide" or "protein" polymers or chains.

"Amino acids" are organic compounds that combine to form proteins. Amino acids are typically classified as either essential, nonessential, and conditional. Essential amino acids cannot be made by the reference body, typically a human body. As a result, they must come from food. The nine essential amino acids for humans are: histidine, isoleucine, leucine, lysine, methionine, phenylalanine, threonine, tryptophan, and valine. "Nonessential" means that the body, such as the human body, produces an amino acid, even if it is not obtained from the food we eat. Nonessential amino acids include alanine, asparagine, aspartic acid, and glutamic acid. Conditional amino acids are usually not essential, except in times of illness and stress; for humans, these include arginine, cysteine, glutamine, tyrosine, glycine, ornithine, proline, and serine.

In some aspects of the disclosure, the AMBR microviscometer is used to detect the synthesis or the average size of a protein. Proteins are understood in the art and include without limitation an antibody, an enzyme, a structural polypeptide and a hormone. Regardless of the protein of interest, the methods of the disclosure are amenable to determining their concentration over time as they are being synthesized, either via in vitro transcription and/or translation, or in vivo. Thus, in some aspects it is contemplated that a magnetic particle of the disclosure detects the synthesis of a protein inside a cell.

Proteins of the present disclosure may be either naturally occurring or non-naturally occurring.

Naturally occurring proteins include, without limitation, biologically active proteins (including antibodies) that exist in nature or can be produced in a form that is found in nature by, for example, chemical synthesis or recombinant expression techniques. Naturally occurring proteins also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure.

Non-naturally occurring proteins are prepared, for example, using an automated polypeptide synthesizer or, alternatively, using recombinant expression techniques using a modified polynucleotide that encodes the desired protein.

As used herein a "fragment" of a protein is meant to refer to any portion of a protein smaller than the full-length protein expression product.

As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, pegylation, and/or polysialylation, and such modifications are also detectable using the methods of the disclosure.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest. A "peptide," as is understood in the art, is generally shorter than a protein.

Carbohydrates

Carbohydrates, such as mono-, oligo-, and poly-saccharides, are contemplated by the disclosure to be an analyte capable of being detected by the methods herein.

Carbohydrates such as oligosaccharides include any carbohydrates comprising between about two to about ten monosaccharides or more connected by either an alpha- or beta-glycosidic link. Oligosaccharides are found throughout nature in both the free and bound form.

Lipids

Also contemplated by the disclosure are methods comprising the detection of lipids. Lipid and phospholipid-derived hormones are contemplated for use in the methods of the disclosure, and these compounds derived from lipids such as linoleic acid and arachidonic acid and phospholipids. The main classes are the steroid hormones that derive from cholesterol and the eicosanoids.

EXAMPLES

Example 1

Reagents.

Solutions used in the viscosity test were purchased from Sigma-Aldrich, unless otherwise specified. Samples tested in the experiment include glycerol and water solutions, lambda DNA EcoRI digest with lengths of 3530-21226 base pairs (bp), and pUC18 HaeIII digest with lengths of 80-587 bp. Magnetic beads with diameters of 7.6, 16 and 45 µm were purchased from Spherotech Inc.

In digestion reactions and PCR amplifications, lambda DNA was used as the template and purchased from Life Technologies. The restriction enzymes EcoRI with EcoRI buffer and PvuI with NEBuffer 3 were purchased from New England Biolabs. For PCR, the forward primer is 5'-GGT-GCTTTATGACTCTGCCGC-3' (SEQ ID NO: 1), and the reverse primer is 5'-CGGCACTGGCAAGCAACTGA-3' (SEQ ID NO: 2). Both primers were purchased from Integrated DNA Technologies. PCR master mix was purchased from Promega.

Viscosity Measurement.

The magnetic beads were washed with water three times and a concentrated bead solution was added to the samples (with 0.2% bovine serum albumin as a non-specific blocking agent). The bead concentration in the sample solution was 0.0075% w/v. The sample solution was rapidly mixed and then placed between two glass slides. The microviscometer works with very small liquid volumes (less than 10 µL). Double-sided tape was inserted between the two glass slides, and nickel particles (210-420 µm) were placed on the edges of the tape to ensure a minimum gap of 210 µm between the two glass slides. Finally, silicone sealant (Dow Corning) was applied to the exterior edges to prevent sample evaporation.

Figure 2:
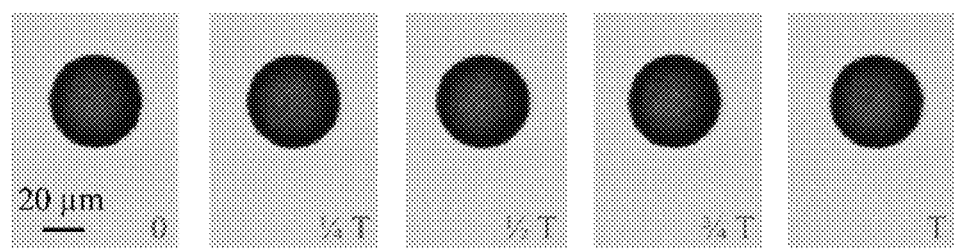
FIG. 2 shows images of the bead rotation at time 0, ¼T, ½ T, ¾T and T for 45 µm beads at 100 Hz driving frequency, where T is the bead rotation period. While the commercial beads look spherical and symmetrical by eye, the software can tell the subtle difference in shape and surface smoothness of the beads, so as to determine the bead rotation periods.
Figure 3A:
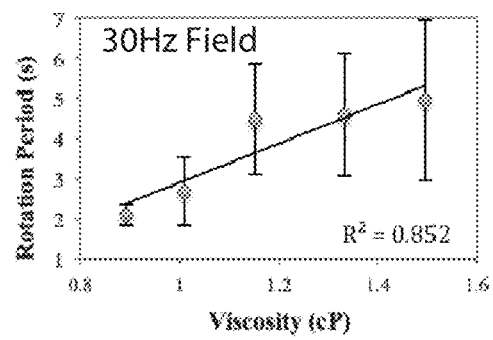
FIG. 3A: 30 Hz.
Figure 3B:
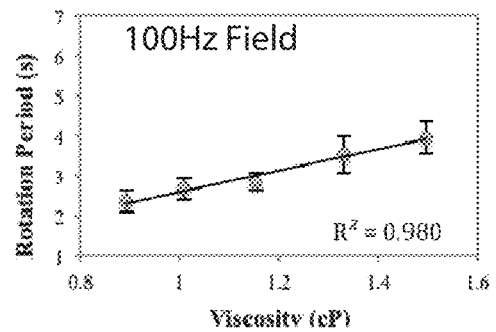
FIG. 3B: 100 Hz.
Figure 3C:
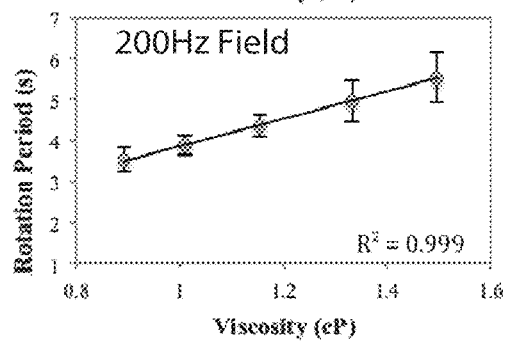
FIG. 3C: 200 Hz.
Figure 3D:
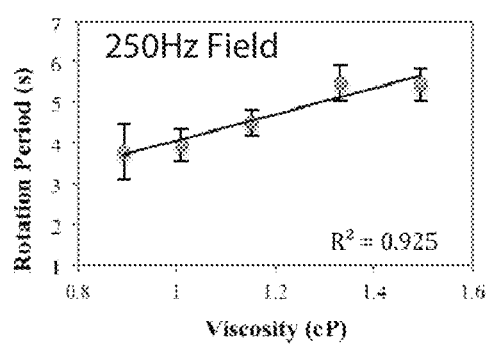
FIG. 3D: 250 Hz. The critical frequency is at 10-15 Hz. The error bars represent the standard deviation among ten different beads in one measurement. The calibration curves yield good linearity consistently at frequencies away from the critical frequency, i.e., from 100 Hz to 250 Hz.

The glass slides were placed in a planar observation area confined within a controlled magnetic field. The latter was generated using orthogonal Helmholtz coils (FIG. 1(a)). Viscosity measurements with an AMBR microviscometer were conducted at 25±1° C. The magnetic field was measured with a 3-axis magnetic field probe (C-H3A-2m; Senis GmbH, Switzerland). The field strength was 2.7 milliTesla (mT) and a driving frequency was as specified for each experiment, both of which were controlled with a custom LabVIEW program. Image stacks of bead rotations were recorded (FIG. 2) during the experiment at a rate of 10 frames per second. Rotation periods of ten randomly selected beads were recorded for each sample, to accommodate the wide variance in commercial bead properties. The image stacks were analyzed using ImageJ, and a plot of image intensity versus image number was generated by ImageJ. The plot was imported into MATLAB, and the periodicity of the bead rotation was determined by applying a fast Fourier transform.

The viscosities of glycerol and water solutions at 25° C. were verified using an Ubbelohde viscometer. Briefly, 15 mL glycerol and water solution were poured into an Ubbelohde viscometer that was immersed in a water bath. The time that it took to pass through two calibrated marks on the viscometer was measured and used to determine the solution viscosity.

Example 2

Calibration of AMBR Viscometer.

Figure 1C:
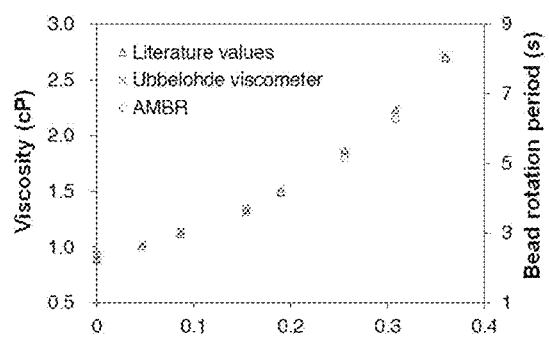
FIG. 1(c) Viscosity measurement of glycerol/water mixture solutions. The graph compares AMBR results in a magnetic field with 100 Hz driving frequency to published values and conventional (Ubbelohde) viscometer measurements of the same liquid.
Figure 1B:
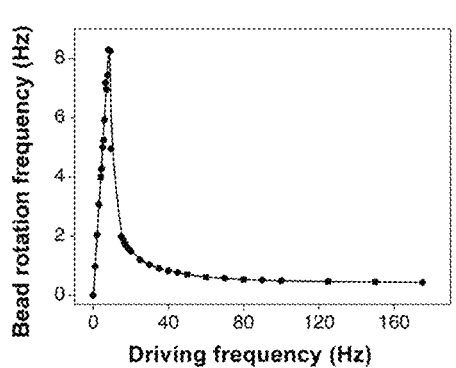
FIG. 1(b) Observed bead rotation frequency vs. field driving frequency. Below 9 Hz the bead rotation frequency matches that of the field; above 9 Hz, the bead rotates asynchronously, with frequency decreasing as the driving frequency increases.
Figure 1D:
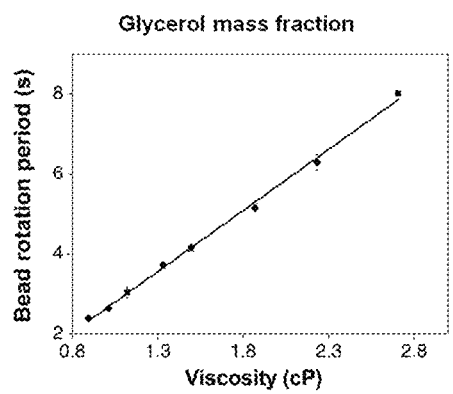
FIG. 1(d) AMBR microviscometer linear response to viscosity in prepared solutions of glycerol/water. Error bars represent standard deviation among three measurements.
Figure 4A:
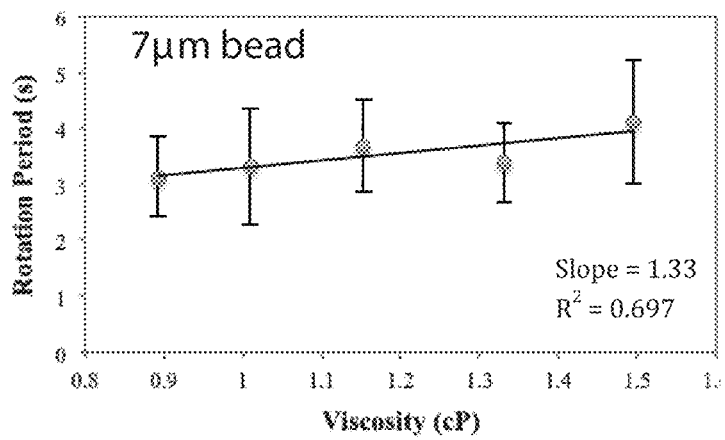
FIG. 4A: 7 µm.
Figure 4B:
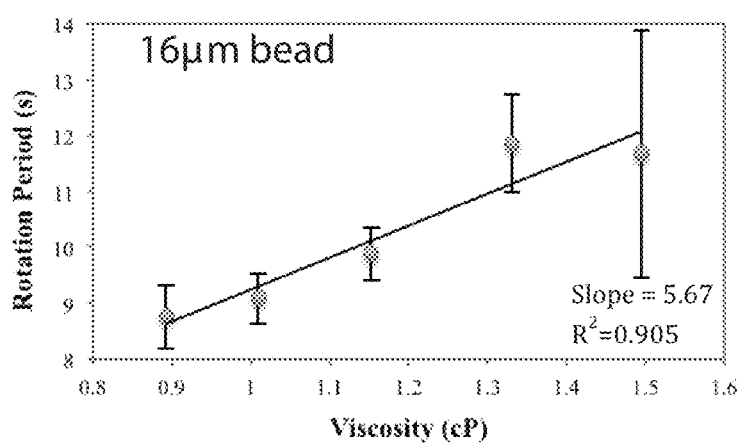
FIG. 4B: 16 µm.
Figure 4C:
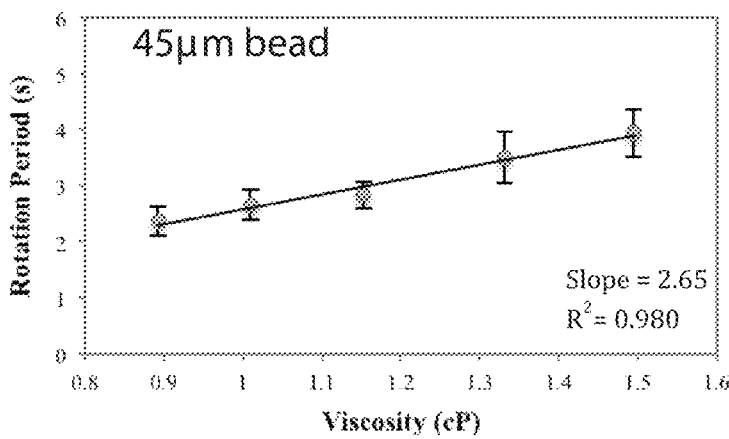
FIG. 4C: 45 µm. Error bars represents standard deviation among 10 beads in one measurement.

A linear relationship was found between the solution viscosity and the rotation period of the bead in the solution. A series of glycerol/water solutions with varying glycerol mass fraction were analyzed by the AMBR microviscometer and, in parallel, with an Ubbelohde viscometer [Cragg et al., Can. J. Chem. 39(1): 203-215 (1961)]. The microviscometer results matched both the Ubbelohde viscosity values and the theoretically predicted values for the mixtures over a viscosity range from 0.89 to 2.8 centipoise (cP) (FIG. 1(c)) [Sheely, Industrial & Engineering Chemistry 24(9): 1060-1064 (1932)]. A correlation curve relating the bead rotation period with the solution viscosity was constructed and yielded excellent uniformity (FIG. 1(d)). The experimentally observed linear relationship between rotation and viscosity agrees well with the theory developed for the paramagnetic AMBR system [Kinnunen et al., Biosens. Bioelectron. 26(5), 2751-2755 (2011)]. Additionally, the linear correlation is robust to variation in the magnetic field driving frequency (FIG. 3), and for three different bead sizes tested, with the 45 µm beads giving optimal linear correlation results (FIG. 4). The slope of the curve as defined by Equation (3) increases with decreasing magnetic responsiveness of the magnetic beads and increasing bead sizes (FIG. 4). The magnetic responsiveness takes into account a combination of factors, such as the volume of the magnetic content and the magnetic susceptibility, as defined in Equation (3). The data show that a smaller magnetic responsiveness gives a larger rotation period, under the same field, resulting in a larger slope (compare FIG. 4B with FIGS. 4A and 4C); also a bigger bead size improves the sensitivity of the viscometer, when the magnetic responsiveness is about the same (compare FIGS. 4A and 4C). These experimental observations are in agreement with the theoretical predictions indicated by Equation (3) (see below).

However, the linearity does not hold as well for a frequency close to the instability threshold, as shown in FIG. 3. Furthermore, the measurement of rotation period is not as reliable, because the jerky motion affects the image analysis.

The observed linear correlation between solution viscosity and bead rotation period can be explained by the nonlinear magnetic oscillation theoretical framework [Kinnunen et al., Biosens. Bioelectron. 26(5): 2751-2755 (2011); McNaughton et al., Sens. Actuators, B 121(1): 330-340 (2007); Sinn et al., Lab Chip 11(15): 2604-2611 (2011); Helgesen et al., Phys. Rev. A 42(12): 7271-7280 (1990); Helgesen et al., Phys. Rev. Lett. 64(12): 1425-1428 (1990)]. At a low driving frequency, the bead rotates at the same rate as the driving magnetic field. However, as the driving frequency increases, the bead cannot overcome the viscous drag exerted by the surrounding fluid, and thus cannot follow the rotating magnetic field. The bead then rotates slower, and asynchronously, with respect to the driving magnetic field (FIG. 1(b)) [Kinnunen et al., Biosens. Bioelectron. 26(5): 2751-2755 (2011); Sinn et al., Lab Chip 11(15): 2604-2611 (2011); Helgesen et al., Phys. Rev. Lett. 64(12): 1425-1428 (1990); Chevry et al., Phys. Rev. E 88(6): 062306 (2013); Frka-Petesic et al., J. Magn. Magn. Mater. 323(10): 1309-1313 (2011); Tokarev et al., Langmuir 28(26): 10064-10071 (2012)]. The nonlinear oscillation only occurs in the asynchronous regime. In a low Reynolds number environment, the force balance between the magnetic torque and the viscous drag yields the relationship between the bead rotation period and the solution viscosity. The effects of interaction between the magnetic bead and the solid surface can be neglected under the experimental conditions described herein. For a paramagnetic bead, the magnetic torque due to the induced magnetic dipole can be expressed as [Kinnunen et al., Biosens. Bioelectron. 26(5): 2751-2755 (2011)], $$\Gamma_{mag}=(\chi''V_m B^2)/\mu_0 \quad \text{Equation (1)}$$

where $\chi''$ is the imaginary part of the magnetic susceptibility (which is frequency dependent), $V_m$ is the volume of the bead's magnetic content (i.e., the magnetic nanoparticles embedded in the bead), B is the strength of the driving magnetic field, and $\mu_0$ is the permeability of free space. The torque due to the viscous drag can be expressed as, $$\Gamma_{vis}=-\kappa\eta V d\theta/dt \quad \text{Equation (2)}$$

where $\theta$ is the arc length of the rotation, $\kappa$ is the shape factor of the bead ($\kappa=6$ for a sphere), $\eta$ is the solution viscosity, and V is the volume of the magnetic bead. By combining Equations (1) and (2), the equation becomes, $$T/\eta=(2\pi\mu_0\kappa V)/(\chi''V_m B^2) \quad \text{Equation (3)}$$

Therefore, in the asynchronous regime, the rotation period of a paramagnetic bead, under the rotating field of a given strength and frequency, is expected to be linearly proportional to the solution viscosity, i.e., $T\propto\eta$. The experimentally observed results confirm this theoretical relationship.

Example 3

To advance the practical utility of the asynchronous rotation method, the influence of the variation in bead properties on bead rotation periods was investigated. A relative standard deviation of approximately 10% is observed due to the variation in bead properties, such as size and magnetic content. As shown in FIG. 5(a), the rotation periods of 20 beads in the same solution do not show a clear bead-size dependency. Thus, bead-size non-uniformity is not the primary contributor to the variation in the rotation period measurement, despite the expected correlation in Equation (3). More likely, the bead magnetic properties, such as magnetic volume and susceptibility, are more significant for the inter-bead variation than is the size variation. The scattered pattern in FIG. 5(a) supports the averaging over multiple beads in the construction of correlation curves and viscosity measurement experiments.

To confirm that inter-bead variation in the rotation period is primarily due to inherent bead properties, the rotation period of the same bead was continuously measured over time. The differences in rotation period over time are much smaller than the differences between two beads in the same experiment (FIG. 5(b)). The relative standard deviation for a single bead over time is approximately 1%, 10 times smaller than the standard deviation in the rotation period among 10 beads. Therefore, the observed measurement error is smaller than the error caused by bead non-uniformity. A wide variation in commercial bead properties has been observed before [Connolly et al., Bio-Med. Mater. Eng. 15(6): 421-431 (2005); Sinn et al., Appl. Phys. Lett. 98(2): 024101 (2011)]; consequently, improved uniformity of bead magnetic character and size is expected to give better sensitivity in viscosity measurement.

Example 4

Preparation of Digestion Reaction Samples.

In the digestion reactions, the restriction enzymes, the corresponding buffers, lambda DNA and nuclease-free water were mixed and incubated at 37° C. for 1 hour. After the reaction, the solutions were placed in a 25° C. water bath before being measured by the AMBR microviscometer.

Preparation of PCR Samples.

All the reagents were added and mixed, and then distributed, 50 µL of the mixture to each tube. The tubes were capped during the reaction to prevent evaporation. Two tubes were used as the product of cycle 0, and the rest were put into a thermal cycler (Bio-Rad). The thermal cycling involved an initial denaturation at 95° C. for 30 seconds, followed by six amplification cycles. The thermal cycles were: 95° C. for 30 seconds (denaturation), 60° C. for 1 minute (annealing), 72° C. for 5 minutes (extension). Then, the reactions were stopped and held at 4° C. Two tubes of samples were taken out from the thermal cycler, and labeled as cycle 6. The rest of the samples underwent resumption of the reaction with an additional five cycles. This was repeated until a total of 41 cycles was completed for the last two tubes of samples. All the samples extracted from different cycles of the reaction were stored in a −20° C. freezer, and placed in a 25° C. water bath before AMBR measurement or gel electrophoresis.

Gel Electrophoresis.

Gel electrophoresis was used to verify the DNA solution results measured by the AMBR microviscometer. A 0.8% agarose gel was prepared, and 1 µL reaction solution was diluted and loaded onto the gel. The gel electrophoresis was conducted in a 1×TBE buffer at 10 V/cm for 2 hours. The fluorescent signal intensities of the 4500 bp bands were estimated with ImageJ.

Viscosity Measurement of DNA Aqueous Solutions.

There is a linear relationship between the viscosity of common diagnostic reaction solutions and the concentration of DNA in those solutions. At a fixed temperature, the relationship between the solution viscosity, $\eta$, and the DNA concentration, C, for a very dilute solution can be expressed as $\eta=\eta_0 (1+C[\eta])$, where $\eta_0$ is the viscosity of the solvent and $[\eta]$ is the intrinsic viscosity of the DNA product. This equation gives a linear correlation between the viscosity and the macromolecule concentration. The intrinsic viscosity increases with the molecular weight of dsDNA, and this correlation has been documented [Tsortos et al., Biopolymers 95(12): 824-832 (2011)], $$[\eta]=3.5*10^{-6} \times MW_{DNA}^{1.05}, 7 \times 10^3 \leq MW_{DNA} \leq 2 \times 10^6$$

$$[\eta]=8.0*10^{-4} \times MW_{DNA}^{0.690}, 2 \times 10^6 \leq MW_{DNA} \leq 8 \times 10^{10}$$

The linear relationship between the viscosity and the DNA concentration breaks down at very high molecular weight or high concentration due to the non-Newtonian property of the DNA solution [Heo et al., J. Rheol. 49(5): 1117 (2005)].

Digestion of DNA with EcoRI has a variety of uses and performs a selective cleaving of DNA at a specific site, forming DNA fragments of length 3530, 4878, 5643, 5804, 7421 and 21226 bp from lambda DNA of original length of 48502 bp. With the experimental relationship given in FIG. 1(c), the viscosities of the DNA EcoRI digest solutions were estimated, at different concentrations, using the measured bead rotation periods. A linear relationship was found between the solution viscosity and the DNA concentration (Table 1 and FIG. 6(a)), confirming the assumption that these solutions were in the dilute solution range. The viscosities of the DNA solutions measured using the AMBR microviscometer are within the theoretically estimated upper and lower bounds.

TABLE 1

Rotation periods and viscosities of lambda DNA EcoRI digest of different DNA concentrations measured by AMBR microviscometer. The expected ranges of viscosities are calculated, assuming only the longest or shortest piece of DNA is present.

| DNA Conc. (g/L) | Experimental Results | | Expected Range | |
|---|---|---|---|---|
| | Rotation Period (s) | Viscosity (cP) | Min Viscosity (cP) | Max Viscosity (cP) |
| 0.00 | 2.40 ± 0.24 | 0.90 ± 0.05 | 0.89 | 0.89 |
| 0.02 | 2.70 ± 0.64 | 0.96 ± 0.14 | 0.94 | 1.07 |
| 0.05 | 3.12 ± 0.62 | 1.06 ± 0.14 | 1.02 | 1.34 |
| 0.09 | 3.87 ± 0.21 | 1.22 ± 0.05 | 1.15 | 1.78 |
| 0.19 | 5.86 ± 0.49 | 1.67 ± 0.11 | 1.41 | 2.67 |
| 0.35 | 9.52 ± 1.53 | 2.48 ± 0.34 | 1.85 | 4.18 |

Measurement of DNA Reaction Progression.

Measurements of restriction digestion samples confirm that the AMBR microviscometer is sensitive to viscosity changes caused by the DNA size changes. As shown in FIG. 6(b), a clear difference in bead rotation period can be seen between the digested and undigested lambda DNA solutions. Thus, the AMBR microviscometer can detect DNA sequence variation using a site-specific restriction endonuclease to essentially alter the solution viscosity.

Figure 7:
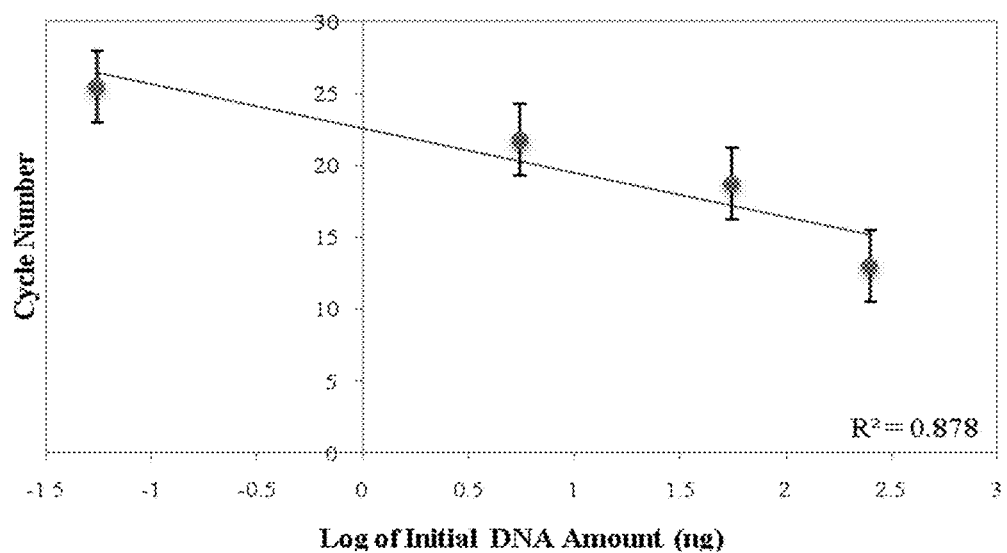
FIG. 7 is a plot of reaction cycle number versus log of initial DNA amount for the qPCR measurement by AMBR method. Error bars represent the uncertainty due to the AMBR measurement of every five cycles.

Measurements of PCR samples over the course of the reaction show that the AMBR microviscometer can detect the formation of PCR products in real time. As expected, the reactions with the higher initial template concentration reach the maximum product concentration sooner than those with lower template concentrations (FIG. 6(c)), and the plot of reaction cycle number versus log of initial DNA concentration yields a linear correlation (FIG. 7). Comparing the AMBR measurements with the gel electrophoresis results on the same samples (FIG. 6(d)) confirms that the viscosity-based method is approximately 5 cycles delayed, relative to gel electrophoresis detection.

Using commercial paramagnetic beads, the AMBR microviscometer is found to be sensitive to the viscosity changes associated with DNA reactions. The results on PCR, with a product size of 4500 bp, yielded a 10% relative error in the rotation period measurement. The AMBR microviscometer is able to detect PCR product sizes that are about 1000 bp, assuming a conversion of more than 95% of dNTPs to polymerized product (i.e., 0.42 g/L final product concentration). However, this sensitivity can be further improved so as to meet the need of monitoring DNA reactions with smaller viscosity changes (e.g., PCRs with shorter DNA products) by optimizing the bead size, shape, temperature, vibration, and magnetic properties. Based on the 1% relative error observed for single-bead measurements, over time, the AMBR microviscometer is able to detect PCR with product size as low as 50 bp. By measuring the changes in viscosity of DNA solutions, the methods disclosed herein can measure either the difference in molecular length for a known concentration or the difference in concentration for a known length.

In summary, the viscosity-based approach using an AMBR microviscometer introduces a new option for label-free DNA detection and for reaction monitoring. In the viscosity range of common DNA reactions, the measurement is completed within one minute, and a typical AMBR microviscometer set-up allows continuous, real-time measurement during the course of any reaction. This viscometer requires only a small amount of sample, and volumes in the picoliter range are accessible if integrated into a microfluidic device. A laser-photodiode apparatus can easily replace the microscope detection setup used in this work, so as to make the measurement more cost-effective [Hecht et al., Biosens. Bioelectron. 48: 26-32 (2013)]. Although demonstrated with DNA solutions, the viscosity-based technology described here can be applied to any polymer reaction or degradation system, as used in the broadest sense of the term "polymer" to refer to conventional chemical polymers and to such aggregations and dis-aggregations as would be found in cell-cell interactions. The improved understanding provided herein of the AMBR microviscometer performance in complex fluids enables new applications, including without limitation mapping the viscosity in living cells, understanding drug delivery mechanisms, and diagnosing blood clotting.

What is claimed is:

1. A method of detecting a chemical change in state of an analyte in a sample comprising:
   (a) contacting the sample with a magnetic particle;
   (b) measuring a first instantaneous non-linear rotation rate of the magnetic particle in the sample at a first time; and
   (c) measuring a second instantaneous non-linear rotation rate of the magnetic particle in the sample at a second time;
   wherein a difference between the first instantaneous rotation rate relative to the second instantaneous rotation rate indicates a change in viscosity in the sample, which indicates the change in state of the analyte in the sample,
   wherein the chemical change in state is selected from the group consisting of nucleic acid synthesis, protein synthesis, nucleic acid hydrolysis, nucleic acid ligation, and protein hydrolysis.

2. The method of claim 1 wherein the analyte is a monomer of a biopolymer.

3. The method of claim 1 wherein the analyte is selected from the group consisting of a cell, a nucleic acid, a protein, a carbohydrate, a lipid, and an amino acid.

4. The method of claim 1 wherein the nucleic acid synthesis is by polymerase chain reaction (PCR).

5. The method of claim 1 wherein the protein synthesis is by in vitro translation.

6. The method of claim 1 wherein the protein synthesis occurs in a cell.

7. The method of claim 1 wherein the nucleic acid hydrolysis is catalyzed by a type I or a type II restriction endonuclease.

8. The method of claim 1 wherein the chemical change is formation or loss of a nucleic acid hybrid, a blood clot, or a ligand-receptor interaction, a nucleic acid-protein interaction, a protein-lipid interaction, a protein-carbohydrate interaction, an antibody-antigen interaction.

9. The method of claim 2 wherein the change in viscosity indicates a change in concentration of analyte in the sample.

10. The method of claim 2 wherein the change in viscosity indicates a change in average length of analyte in the sample.

11. The method of claim 1 wherein the change in viscosity is measured in real time.

12. The method of claim 1 wherein the change in viscosity is from about 0.01 centipoise (cP) to about 10 cP.

13. The method of claim 12 wherein the change in viscosity is from about 0.1 cP to about 2 cP.

14. A method of detecting a chemical change in state of an analyte in a sample comprising:
   (a) contacting the sample with a magnetic particle;
   (b) measuring a first instantaneous non-linear rotation rate of the magnetic particle in the sample at a first time; and
   (c) measuring a second instantaneous non-linear rotation rate of the magnetic particle in the sample at a second time;
   wherein a difference between the first instantaneous rotation rate relative to the second instantaneous rotation rate indicates a change in viscosity in the sample, which indicates the change in state of the analyte in the sample,
   wherein the chemical change in state is catalyzed by an enzyme.

15. The method of claim 14 wherein the analyte is a monomer of a biopolymer.

16. The method of claim 14 wherein the analyte is selected from the group consisting of a cell, a nucleic acid, a protein, a carbohydrate, a lipid, and an amino acid.

17. The method of claim 14 wherein the enzyme is selected from the group consisting of a polymerase, a nuclease, a hydrolase, a lyase, an oxidase, a peptidase, and a ligase.

18. The method of claim 14 wherein the chemical change is formation or loss of a nucleic acid hybrid, a blood clot, or a ligand-receptor interaction, a nucleic acid-protein interaction, a protein-lipid interaction, a protein-carbohydrate interaction, an antibody-antigen interaction.

19. The method of claim 15 wherein the change in viscosity indicates a change in concentration of analyte in the sample.

20. The method of claim 15 wherein the change in viscosity indicates a change in average length of analyte in the sample.

21. The method of claim 14 wherein the change in viscosity is measured in real time.

22. The method of claim 14 wherein the change in viscosity is from about 0.01 centipoise (cP) to about 10 cP.

23. The method of claim 22 wherein the change in viscosity is from about 0.1 cP to about 2 cP.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:

-continued

```
<223> OTHER INFORMATION: Synthetic Polynucleotide

<400> SEQUENCE: 1
ggtgctttat gactctgccg c                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
cggcactggc aagcaactga                                                20
```